United States Patent
Bytow (10) Patent No.: US 8,098,923 B2
(45) Date of Patent: Jan. 17, 2012

(54) SHEET METAL PROCESSING EXAMINATION

(75) Inventor: Peter Bytow, Simmozheim (DE)

(73) Assignee: TRUMPF Werkzeugmaschinen GmbH + Co. KG, Ditzingen (DE)

( * ) Notice: Subject to any disclaimer, the term of this patent is extended or adjusted under 35 U.S.C. 154(b) by 979 days.

(21) Appl. No.: 12/047,662

(22) Filed: Mar. 13, 2008

(65) Prior Publication Data

US 2008/0226155 A1    Sep. 18, 2008

(30) Foreign Application Priority Data

Mar. 16, 2007    (EP) .................................... 07005442

(51) Int. Cl.
G06K 9/00    (2006.01)
B26D 7/06    (2006.01)

(52) U.S. Cl. .......................................... 382/141; 83/129

(58) Field of Classification Search .................. 382/141; 83/129; 356/237.1, 430, 431, 433, 448, 625, 356/635
See application file for complete search history.

(56) References Cited

U.S. PATENT DOCUMENTS

| | | | |
|---|---|---|---|
| 3,636,362 A * | 1/1972 | Beeman et al. | 356/626 |
| 3,806,252 A * | 4/1974 | Harris et al. | 356/626 |
| 4,857,698 A | 8/1989 | Perun | |
| 5,184,217 A * | 2/1993 | Doering | 348/88 |
| 5,615,471 A * | 4/1997 | Perazzolo | 29/560 |
| 5,721,587 A | 2/1998 | Hirose | |
| 6,041,271 A * | 3/2000 | Lindstrom | 700/175 |

FOREIGN PATENT DOCUMENTS

| | | |
|---|---|---|
| EP | 0536685 | 4/1993 |
| JP | 2006030010 | 2/2006 |
| WO | WO 99/10136 | 3/1999 |

OTHER PUBLICATIONS

Office Action from corresponding European Patent Application No. 07 005 442.4 with English translation, mailed Dec. 3, 2009, 7 pages.
International Search Report from corresponding European Application No. 07005542, mailed Jul. 12, 2007, English translation included, 13 pages.

* cited by examiner

*Primary Examiner* — Michael A Lyons
(74) *Attorney, Agent, or Firm* — Fish & Richardson P.C.

(57) ABSTRACT

For examining a metal sheet processing operation, a method includes scanning a detection beam along a processed metal sheet by causing a relative movement between the detection beam and the processed metal sheet, during the scanning, determining a position of an edge of the metal sheet hole by monitoring the detection beam, determining, from the determined hole edge position, a geometric configuration of the metal sheet hole, performing a comparison of the determined geometric configuration of the metal sheet hole with a corresponding desired hole configuration; and then sending a signal indicating information about the metal sheet processing operation, based upon the comparison.

18 Claims, 5 Drawing Sheets

FIG. 5C

SHEET METAL PROCESSING EXAMINATION

CROSS REFERENCE TO RELATED APPLICATION

This application claims priority under 35 U.S.C. §119(a) from EP Application No. 07 005 442.4, filed Mar. 16, 2007, the entire contents of which are hereby incorporated by reference.

TECHNICAL FIELD

The invention relates to examining a metal sheet processing operation in respect of the presence of regular conditions during operation, such as by examining the quality of edges of a hole formed by the operation.

BACKGROUND

U.S. Pat. No. 5,721,587 discloses a revolver punching press having an upper tool revolver and having a lower tool revolver. When processing workpieces during regular operation, punching tools are used that are positioned in mutually opposite tool receiving members of the two tool revolvers and that cooperate with each other. Before the start of the regular workpiece processing operation, one performs a test processing operation. A video camera and a light source of an image capturing device are mounted in two cooperating tool receiving members for receiving punching tools. After the test processing operation, the workpiece with a punched-out portion is moved into the receiving region of the video camera. Subsequently, the video camera records the punched-out portion, which is back-lit by the light source. Finally, the quality of the punched-out portion is examined by computer-supported evaluation of the recording made of the punched-out portion.

The EP publication EP 0 536 685 A1 discloses examining a quality of a perforation of paper webs with a measurement device, which comprises a light source and a detector device spaced apart from each other. The paper web to be examined is moved through the intermediate space between the light source and the detector device. Light directed from the light source to the detector device passes through the perforations of the paper web and reaches the detector device. This produces, owing to the incidence of light, a detector signal that is supplied to an evaluation unit. If irregular conditions prevail when the perforations are produced, for instance, if the perforation blades used are worn, paper fibers remain in the perforations produced. The more paper fibers project into an illuminated perforation, the lower is the intensity of the light which reaches the detector device and the smaller is a signal stroke of the detector signal which is generated at the detector device owing to the incidence of light. Consequently, the signal stroke of the detector signal allows an observation to be made as to whether the perforation of the paper web has or has not been carried out under regular conditions.

SUMMARY

In one general aspect of the invention, a method of examining a metal sheet processing operation includes scanning a detection beam along a processed metal sheet by causing a relative movement between the detection beam and the processed metal sheet, during the scanning, determining a position of an edge of the metal sheet hole by monitoring the detection beam, determining, from the determined hole edge position, a geometric configuration of the metal sheet hole, performing a comparison of the determined geometric configuration of the metal sheet hole with a corresponding desired hole configuration, and then sending a signal indicating information about the metal sheet processing operation, based upon the comparison.

In another aspect, a method for processing a metal sheet includes processing the metal sheet with a process for generating a metal sheet hole, scanning a detection beam along a processed metal sheet by moving the detection beam and the processed metal sheet relative to each other, monitoring the detection beam having passed a metal sheet hole processed by the metal sheet processing operation, during the scanning, detecting an edge of the metal sheet hole based on detecting the detection beam at a defined position of the detection beam and of the metal sheet, determining a geometric actual state of the metal sheet hole on the basis of the position of the edge, and comparing the determined geometric actual configuration of the metal sheet hole with a corresponding desired configuration, thereby evaluating an operating condition during the previous metal sheet processing operation.

In another aspect, a method of forming desired holes in sheet metal includes forming a hole by a set of hole forming operation parameters, moving a detection beam across an edge of the formed hole to locate the edge based on detecting the detection beam at a defined position of the detection beam and of the metal sheet, determining, from the edge location, a characteristic of the formed hole, making a comparison of the determined characteristic to a desired characteristic, and based upon the comparison, modifying one or more of the hole forming operation parameters for forming a further hole.

In another aspect, a hole forming machine includes a tool operable to form a hole in sheet metal, a beam source operable to direct a hole detection beam across a hole formed by the tool, a beam detector responsive to the hole detection beam to generate a signal indicating beam detection, a hole edge evaluator that receives the signal from the beam detector, determines a position of an edge of the hole and a geometric configuration of the hole, based on the received signal, makes a comparison of the determined geometric hole configuration to a desired configuration, and sends a signal indicative of an undesired state of one or more hole forming operation parameters.

In another aspect, a device for examining an operating condition of a metal sheet processing operation by examining a quality of a metal sheet hole being a result of the metal sheet processing operation, includes a detection device comprising a transmitter and a receiver for transmitting and monitoring a detection beam, respectively, a movement unit for moving the detection beam and the processed metal sheet relative to each other, and an evaluation device connected to the detection device, wherein the detection device is configured to detect an edge of the metal sheet hole at a defined relative position of the detection beam and of the metal sheet, and the evaluation device is configured to determine a geometric actual state of the metal sheet hole and to compare the geometric actual state with a corresponding desired state, thereby evaluating the operation condition of the metal sheet processing operation.

In another aspect, a mechanical production arrangement includes a processing device for producing metal sheet holes in metal sheets, and a device for examining an operating condition of a metal sheet processing operation of the processing device as described above.

In another aspect, a method for examining a metal sheet processing operation includes scanning a detection beam over a processed metal sheet with a metal sheet hole, based on monitoring the detection beam, detecting an edge of the metal sheet hole and identifying a position on the metal sheet corresponding to the detected edge, based on the position of the edge, determining a geometric actual state of the hole, comparing the determined geometric actual state of the metal sheet hole with an desired state being associated with the metal sheet processing operation, and deriving information about the metal sheet processing operation.

Implementations may include one or more of the following features. In some embodiments, the signal can indicate the presence of regular or irregular conditions during the metal sheet processing operation.

In some embodiments, based on the comparison, the quality of the metal sheet hole processed by the metal sheet processing operation can be evaluated.

The detection beam can be a light beam, e.g. a laser beam.

In some embodiments, the detection beam and the processed metal sheet can be moved relative to each other such that a scanned path extends transversely through the metal sheet hole. Then, during scanning, the edge of the metal sheet hole can be detected at points of intersection of the edge of the metal sheet hole with the path. The points of intersection can then be, for example, at opposite sides of the hole.

In some embodiments, an actual extent between the detected points of intersection can be determined. Then, one can compare the determined actual extent of the metal sheet hole with a corresponding desired extent.

In some embodiments, the method can further include examining a quality of a circular metal sheet hole by scanning a path, which extends transversely through the circular metal sheet hole, and detecting points of intersection of the edge of the circular metal sheet hole and the path, wherein the determined geometric configuration of the circular metal sheet hole can be an actual diameter of the circular metal sheet hole given by the distance between the detected points of intersection and wherein the actual diameter of the circular metal sheet hole can be compared with a corresponding desired diameter as a corresponding desired configuration.

In some embodiments, the detection beam can be scanned relative to the processed metal sheet along a path that extends along the edge of the metal sheet hole. Then, at least a partial length of the edge of the metal sheet hole can be detected.

In some embodiments, the geometric actual configuration can be a determined actual configuration of at least a portion of the edge contour of the metal sheet hole.

In some embodiments, the determined geometric actual configuration can be at least one of an actual shape and an actual orientation of at least a portion of the edge contour of the metal sheet hole. For example, the actual shape of the edge contour of the metal sheet hole can be compared with a corresponding desired shape. In addition, or alternatively, an actual orientation can be compared with a corresponding desired orientation.

In some embodiments, making a comparison can include gaining information about the presence or absence of desired conditions during the metal sheet processing operation.

In some embodiments, the method can further include determining a deviation of the determined characteristic from the corresponding desired characteristic, the deviation being indicative for the absence of regular conditions and performing an intervention to correct for the deviation to provide regular conditions for a succeeding metal sheet processing operation.

In some embodiments, forming a hole can include applying a punching tool to the sheet metal for generating the hole and wherein modifying the hole forming operation parameter includes exchanging the punching tool.

In some embodiments, making the comparison can provide information about at least one of the punching tool being the correct punching tool, the punching toll being in an acceptable operating condition, the punching tool being worn, and the punching toll being broken.

In some embodiments, the hole forming machine can further include a control device, which is connected to hole edge evaluator and receives the signal and which is configured to control the tool based on the signal.

In some embodiments, the processing device can includes a punching tool for generating the metal sheet hole, and the device for examining the operating condition is configured to derive information about the operating condition of the punching tool. The information can include, for example, the punching tool being the correct punching tool, the punching tool being in an acceptable operating condition, the punching tool being worn, and the punching tool being broken.

Alternatively, or in addition, the processing device can further include a threading tool for generating a thread in the metal sheet hole, and the device for examining the operating condition can be configured to derive information about the operating condition of the threading tool. The information can include, for example, the threading tool being the correct threading tool, the threading tool being in an acceptable operating condition, the threading tool being worn, and the threading tool being broken.

In a further aspect of the invention, a detection beam allows highly precise detection of an edge of the metal sheet hole to be examined. On the basis of the highly precise detection result, it is possible to establish a geometric actual state of the metal sheet holes in a highly precise manner. By comparing the geometric actual state with a corresponding desired state of the metal sheet holes, the result of the preceding metal sheet processing operation can be examined. As the geometric actual state of the metal sheet holes has been established with a high degree of precision, the comparison with the corresponding desired state can also provide a highly precise result. If a deviation of the established geometric actual state from the corresponding desired state of a metal sheet hole is established based on the comparison, one can take steps within during the production process and/or at a production arrangement in order to make the relevant geometric actual state of the metal sheet hole correspond to the associated desired state. Preferably, the corresponding correction is carried out during ongoing operation and immediately after the detection of the deviation of the geometric actual state from the geometric desired state of the metal sheet hole. In that manner, it is possible to ensure maximum process or operational reliability of the production process and the production arrangement. The production of rejects can be minimized or decreased.

If a light beam is used as the detection beam, it is possible to make use of a large variety of technically developed and highly precisely functioning optical systems and evaluation devices.

In some embodiments, the path of the detected movement, with which the processed metal sheet and the detection beam are moved relative to each other, extends transversely through the metal sheet hole. The parts of the edge of the metal sheet hole that one detects are the intersection points of the edge with the path of the detection movement. The intersection points are mutually opposite along the path of the detection movement.

The intersection points of the edge of the metal sheet hole with the path of the detection movement are particularly apparent and can consequently be detected with great precision. The actual extent of the metal sheet hole between the detected intersection points that is determined can be meaningful in several regards. If an examined metal sheet hole is, for example, the result of a punching metal sheet processing operation, a deviation of the actual extent from the corresponding desired extent of the metal sheet hole can indicate a partial breakage of the punching stamp used. The deviation can also indicate an incorrect orientation of a punching tool used with respect to the axis of the punching stroke or it can indicate the use of a punching tool with the incorrect stamp and/or die cross-section or diameter.

If a thread is formed in a prefabricated metal sheet hole, the metal sheet hole provided with the thread has, owing to the processing operation, a smaller diameter than the prefabricated metal sheet hole. It is possible to determine whether a thread forming operation has produced the desired processing result. The desired result has not been achieved if the measured actual extent of the metal sheet hole is, for example, greater than the associated desired extent. The measurement result that the actual extent of the metal sheet hole corresponds to the actual extent of the prefabricated metal sheet hole to be provided with a thread may be an indication of a fracture of the thread forming tool.

In some embodiments, the metal sheet hole to be examined has a circular cross-section, in which case an incorrect orientation of punching tools with respect to the axis of the punching stroke may be considered irrelevant in punching tools having a circular cross-section.

In some embodiments, the edge contour of the metal sheet hole can be detected in addition or alternatively to the actual extent of the metal sheet hole to be examined along a path of the detection movement that traverses the metal sheet hole. For example, the shape and the orientation of the edge contour of the metal sheet hole can be meaningful. For instance, the measurement result that the actual shape of a metal sheet hole produced by a punching metal sheet processing operation deviates from the corresponding desired shape may indicate, for example, a partial breakage of the punching tool or the use of a punching tool with the incorrect tool cross-section. Determining that the measured actual orientation of the edge contour of the metal sheet hole does not correspond to the associated desired orientation can indicate incorrect orientation of the punching tool with respect to the axis of the punching stroke.

If a deviation of the geometric actual state of the examined metal sheet hole from a corresponding geometric desired state is determined, tone can initiate various steps. For example, tone can produce a signal that causes a machine operator to intervene. One can further initiate an automatic interruption of the production process or automatic stoppage of the production arrangement. In the interests of large automation of the production process and the production arrangement, tone can automatically correct the cause of the determined deviation of the geometric actual state from the geometric desired state of the metal sheet hole examined. For instance, if a partial breakage of the punching tool used is indicated, a tool changing operation can automatically be introduced by the control unit of the production arrangement. With the tool changing operation, the possibly defective punching tool can be exchanged for an operational punching tool. By subsequently examining metal sheet holes, which have been processed with the exchanged punching tool, one can determine whether by changing the tool, the geometric actual state of the examined metal sheet hole has been made to correspond to the relevant desired state.

The details of one or more embodiments of the invention are set forth in the accompanying drawings and the description below. Other features, objects, and advantages will be apparent from the description and drawings, and from the claims.

BRIEF DESCRIPTION OF DRAWINGS

Like reference symbols in the various drawings indicate like elements.

DETAILED DESCRIPTION

Figure 1:
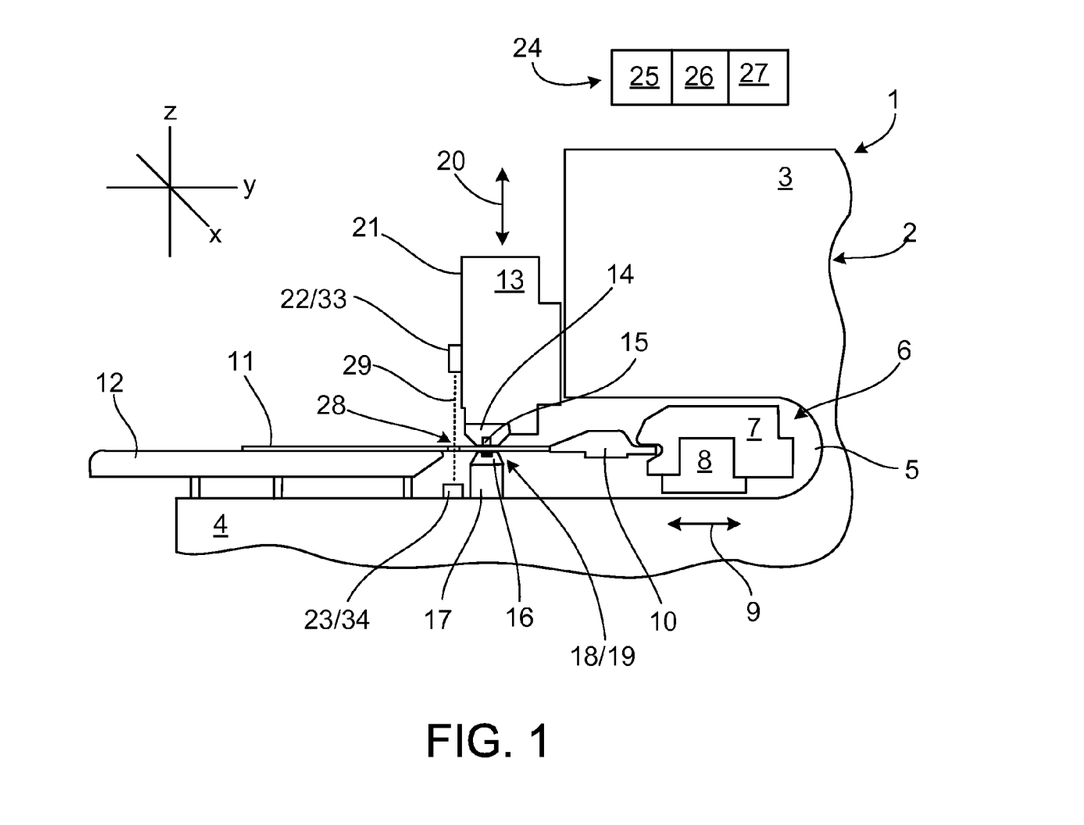
FIG. 1 is a side view of a mechanical arrangement for producing metal sheets with a processing device and with a device for examining the processing result.

In FIG. 1, a mechanical arrangement 1 for producing metal sheets comprises a C-shaped machine frame 2, having an upper frame member 3 and a lower frame member 4. A movement unit in the form of a conventional coordinate guide unit 6 is received in a jaw space 5 of the machine frame 2. A carriage 7 of the coordinate guide unit 6 can be moved along a guide rail 8 perpendicularly to the plane of the drawing of FIG. 1. Together with the guide rail 8, the carriage 7 can be moved on the lower frame member 4 of the machine frame 2 in the directions indicated by a double-headed arrow 9.

At the front side of the carriage 7 of the coordinate guide unit 6 a plurality of clamping claws 10 are provided, one of which is shown in FIG. 1. The clamping claws 10 conventionally clamp the edge of a workpiece, which is to be processed by means of the mechanical arrangement 1. The workpiece can be a metal sheet 1. The metal sheet 11 is further supported on a metal sheet support 12, which is attached to the lower frame member 4 of the machine frame 2. The metal sheet 11 can be moved in a horizontal plane owing to the described mobility of the carriage 7 of the coordinate guide unit 6.

The mobility of the metal sheet 11 can be used in particular for processing metal sheets. In the embodiment illustrated in FIG. 1, for processing the metal sheets, a press device 13 is provided at the free end of the upper frame member 3 of the machine frame 2. The press device 13 has an upper tool receiving member 14 that receives a schematically indicated punching stamp 15. An also schematically indicated punching die 16 is associated with the punching stamp 15 and provided in a lower tool receiving member 17 of the lower frame member 4 of the machine frame 2. Together with the punching stamp 15, the punching die 16 represents a processing device in the form of a punching tool 18. Instead of the punching tool 18, a thread forming tool 19 can be provided as the processing device. The respective tool members are mounted in the upper tool receiving member 14 and the lower tool receiving member 17.

A press drive (not illustrated in detail) of the press device 13 raises and lowers the upper tool receiving member 14 with the tool member mounted thereon in a lifting direction 20 along a double-headed arrow. A housing 21 of the press device 13 remains stationary during the lifting movement of the upper tool receiving member 14.

At the side facing away from the coordinate guide unit 6, the housing 21 of the press device 13 is provided with a transmission and reception unit 22. A reflector 23, is mounted to the lower frame member 4 of the machine frame 2 and forms a detection device together with the transmission and reception unit 22. The reflector is located opposite the transmission and reception unit 22. The coordinate guide unit 6, the press device 13, and the transmission and reception unit 22 are connected to a control computer 24 of a numerical control unit for the mechanical arrangement 1. The transmission and reception unit 22 is connected to an evaluation device 25 of the control computer 24. The evaluation device 25 is connected to a movement control unit 26 and a press control unit 27. The drive motors of the coordinate guide unit 6 are controlled by the movement control unit 26 and the press drive of the press device 13 is controlled by the press control unit 27. In this respect, the press control unit 27 is a control device for the punching tool 18 and/or the thread forming tool 19.

In order to process the metal sheet 11 in a punching manner, the punching tool 18 provided for the relevant processing operation is fitted in the upper tool receiving member 14 and the lower tool receiving member 17. Subsequently, the coordinate guide unit 6 positions the metal sheet 11 held by the clamping claws 10, relative to the punching tool 18. If punched-out portions (e.g. metal sheet holes) are intended to be formed in the metal sheet 11, a plurality of operating strokes of the punching tool 18 or different punching tools can be required and the metal sheet 11 is moved by the coordinate guide unit 6 after each individual operating stroke of the punching tool 18.

The sheet metal processing operation can be based on processing parameters e.g. hole forming operation parameters. Those parameters can include, for example, the type of tool, the size and shape of the punched out area, the position and orientation (in 3D) with which a tool is applied. Moreover, the parameters can define a sequence of tool operations and the geometrical change between succeeding applications of the same or of different processing tools.

After the punching processing operation has been finished, the coordinate guide unit 6 moves the processed metal sheet 11 with the punched-out portion produced out of the immediate vicinity of the punching tool 18 into a region in which the punched-out portion is accessible to the transmission and reception unit 22. The examination of the quality of the result of the metal sheet processing operation, e.g. of the quality of the punched-out portion produced, is then carried out.

In FIG. 1, the metal sheet 11 with a previously produced metal sheet hole or punched-out portion 28 is positioned below the transmission and reception unit 22. A transmitter of the transmission and reception unit 22 directs a detection beam, e.g. a laser beam 29, towards the metal sheet 11. The position of the axis of the laser beam 29 is defined in an x-y-z coordinate system, which is used for the numerical control of the mechanical arrangement 1. The current position of the metal sheet 11 and consequently also the current position of the punched-out portion 28 are also defined in an x-y-z coordinate system. In place of the laser beam 29, other types of detection beams, e.g. a red light beam, can also be employed.

Figure 2:
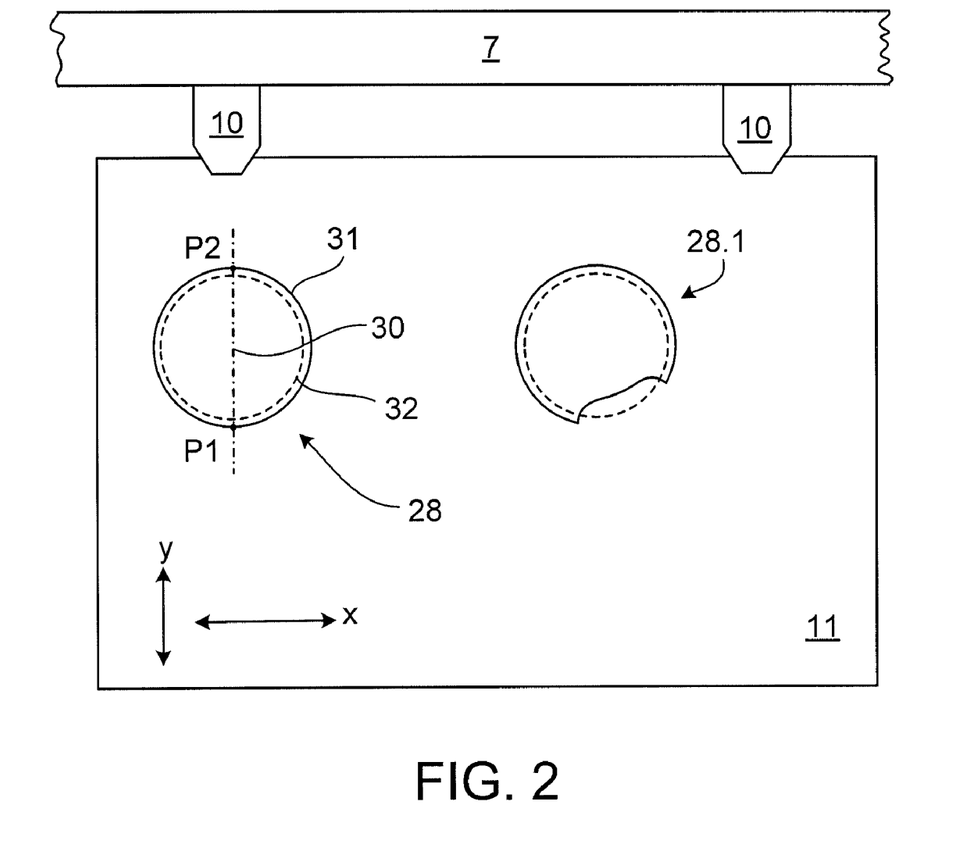
FIG. 2 is an illustration for explaining the operation of the device of FIG. 1 for examining the processing result in a first application.

To examine the result of the preceding metal sheet processing operation, the coordinate guide unit 6 moves the metal sheet 11 with a detection movement in a transverse direction relative to the laser beam 29. In FIG. 2, a path 30 is indicated by dot-dash lines. Along this path 30, the laser beam 29 scans transversely through the punched-out portion 28 during the detection movement on the metal sheet 11.

At the beginning of the detection movement, the laser beam 29 strikes the non-perforated metal sheet 11. In the course of the detection movement, the laser beam 29 reaches the edge 31 of the punched-out portion 28 at a first point of intersection P1 of the edge 31 with the path 30. For the numerical control of the mechanical arrangement 1 or the evaluation device 25 of the control computer 24 connected to the transmission and reception unit 22, the first intersection point P1 is marked in that the laser beam 29 strikes the reflector 23 through the punched-out portion 28 practically when the first intersection point P1 is reached. The reflector 23 is arranged below the metal sheet 11 and reflects the laser beam back to the receiver of the transmission and reception unit 22. At that time at which the laser beam 29 is first reflected back by the reflector 23 and strikes the receiver of the transmission and reception unit 22, the position of the metal sheet 11 is established in the x-y-z coordinate system of the mechanical arrangement 1.

As the detection movement continues, the laser beam 29 scans across the punched-out portion 28 until it reaches a second point of intersection P2 of the edge 31 of the punched-out portion 28 with the path 30. During its movement transversely through the punched-out portion 28, the laser beam 29 is continuously reflected by the reflector 23 to the receiver of the transmission and reception unit 22. The associated light incidence at the receiver of the transmission and reception unit 22 ends as soon as the laser beam 29 reaches the edge 31 of the punched-out portion 28 at the second intersection point P2. The end of the light incidence at the transmission and reception unit 22 marks for the numerical control unit of the mechanical arrangement 1 an operating state at which the position of the metal sheet 11 is again established in the x-y-z coordinate system of the mechanical arrangement 1. Based on the positional change of the metal sheet 11 between the first determination of the position (laser beam 29 at P1) and the second determination of the position (laser beam 29 at P2), the evaluation device 25 derives the actual extent of the punched-out portion 28 between the first intersection point P1 and the second intersection point P2. In FIG. 2, the actual extent corresponds to the diameter of the circular punched-out portion 28. The determined actual extent of the punched-out portion 28 is compared in the evaluation device 25 with a desired extent of the punched-out portion 28 stored in the numerical control unit of the mechanical arrangement 1. That desired extent is defined by the dimensions of the punching tool 18, which was used for producing the punched-out portion 28.

The fact that light emitted from the transmitter has reached the reflector 23 and then the receiver during the detection movement between the metal sheet 11 and the laser beam 29, demonstrates that the preceding processing operation on the metal sheet 11 has produced a workpiece hole. Details of the workpiece hole, e.g. characteristics of the specific geometric configuration, can be obtained by evaluating the changes of the detected detection beam during the detection movement.

The determination of a significant deviation of the actual extent from the desired extent of the punched-out portion 28 by the comparison indicates irregular conditions during the preceding metal sheet punching processing operation. Accordingly, for example, the evaluation device 25 can generate a signal indicating information about the metal sheet processing operation that has taken place. Based on the signal, the processing operation can be modified by, for example, adjusting the processing parameters. Exemplary irregular conditions include the use of an incorrect punching tool 18 during the punching processing of the metal sheet 11, for example, a punching stamp 15 and a punching die 16 with an excessively large diameter. Exemplary irregular conditions include further a partial stamp breakage of the punching tool 18 so that the punched-out portion 28 has been cut only partially. The processing result in the case of a partial stamp breakage can result, for example, in a faulty punched-out portion 28.1 as illustrated in FIG. 2.

If a significant deviation of the actual extent of the punched-out portion 28 from the desired extent is determined, irrespective of the cause, the drive motors of the coordinate guide unit 6 are stopped by the movement control unit 26 and the press drive of the press device 13 is stopped by the press control unit 27. Furthermore, the numerical control unit of the mechanical arrangement 1 generates an error message, which informs the operator about the malfunction which has occurred. Alternatively, or in addition, a message suggesting modifications through the operator or a message showing the performed modifications can be generated.

As an alternative to the path 30, a path 32 of the detection movement of the laser beam 29 along the metal sheet 11 is indicated in FIG. 2.

For clarification, the path 32 is illustrated to be displaced within to the circular edge 31 of the punched-out portion. Actually, the path 32 follows the desired contour of the edge 31 of the punched-out portion 28. During the detection movement, the laser beam 29 scans along the path 32 with its beam axis. Accordingly, a portion of the cross-section of the laser beam 29 passes through the punched-out portion 28 and the other portion of the laser beam cross-section falls on the upper side of the metal sheet 11.

In general, and specifically in this case, one can replace the above-described transmission and reception unit 22 and the associated reflector 23 by a transmission device 33 above the metal sheet 11 and a reception device 34 below the metal sheet 11. The portion of the cross-section of the laser beam 29 that passes through the punched-out portion 28 reaches the reception device 34. The transmission device 33 and reception device 34 form a detection device and are connected to the evaluation device 25 of the control computer 24.

During the detection movement, the path 32 and therefore the desired contour of the edge 31 of the punched-out portion 28 are scanned with the laser beam 29. If the correct portion of the cross-section of the laser beam 29 strikes the reception device 34 during the entire detection movement, then the actual contour of the edge 31 of the punched-out portion 28 seems to be in agreement with the desired contour. Instead, the fact that the laser beam 29 strikes the reception device 34 during the detection movement with one or more interruptions, can indicate a partial stamp breakage and accordingly the presence of a punched-out portion in the manner of the punched-out portion 28.1 as shown, for example, in FIG. 2. Moreover, the fact that no light at all falls on the reception device 34 during the detection movement along the path 32, can indicate an excessively small diameter of the punched-out portion produced or a complete stamp breakage, because of which no workpiece hole has been produced in the region of the metal sheet 11, which should have been processed.

In the event of punched-out portion having a cross-section which deviates from the circular shape, it can additionally be possible to examine whether the punched-out portion is arranged on the metal sheet 11 with its desired orientation. For this purpose, the movement path of the detection movement to be carried out can also extend either transversely through the relevant punched-out portion (FIG. 3) or along the edge of the relevant punched-out portion (FIG. 4).

Figure 3:
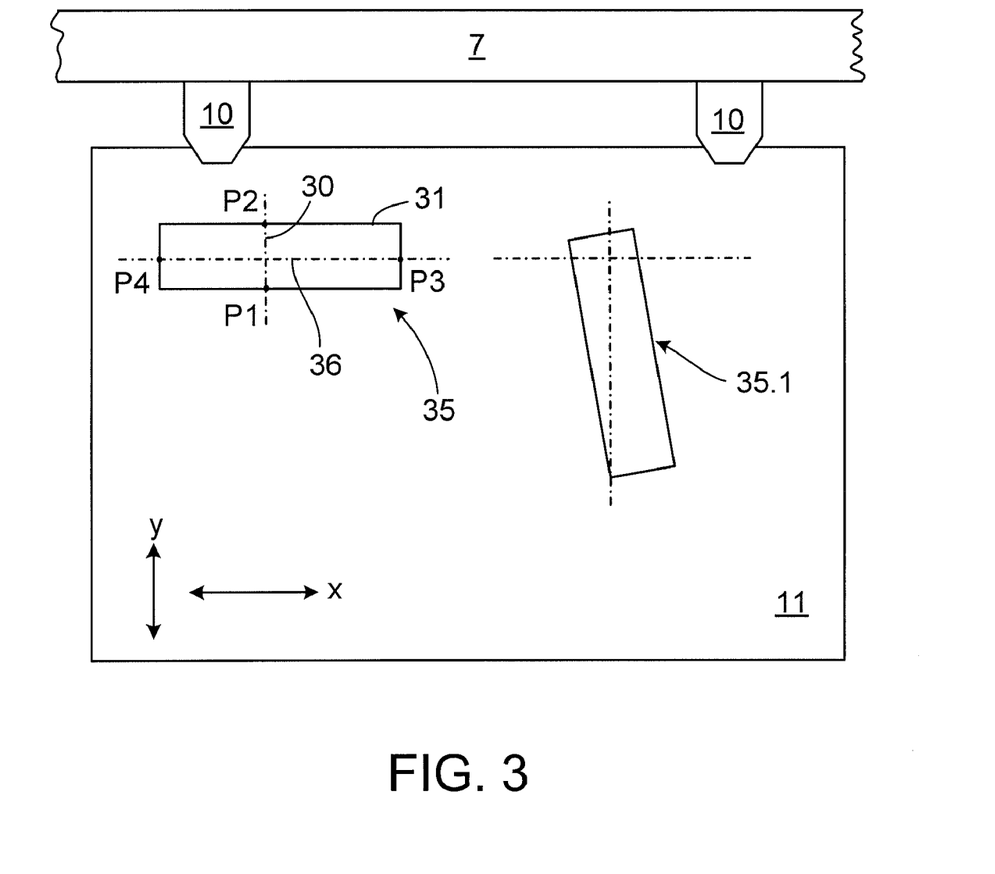
FIG. 3 is an illustration of the operation of the device of FIG. 1 for examining the processing result in a second application.

In the first case illustrated in FIG. 3, the actual extent of a metal sheet hole or punched-out portion 35 between intersection points P1, P2 and/or between intersection points P3, P4 between an edge 31 of the punched-out portion 35 and a movement path 30 or 36 is compared with a corresponding desired extent. As shown in FIG. 3, an incorrect punched-out portion 35.1 can cause a deviation of the established actual extent of the punched-out portion 35 from the desired extent. Such a deviation can indicate incorrect orientation of the punched-out portion 35 with respect to the metal sheet 11. An incorrect orientation of the punching tool 18 can be, for example, the reason for the incorrect orientation of the punched-out portion 35.1.

Figure 4:
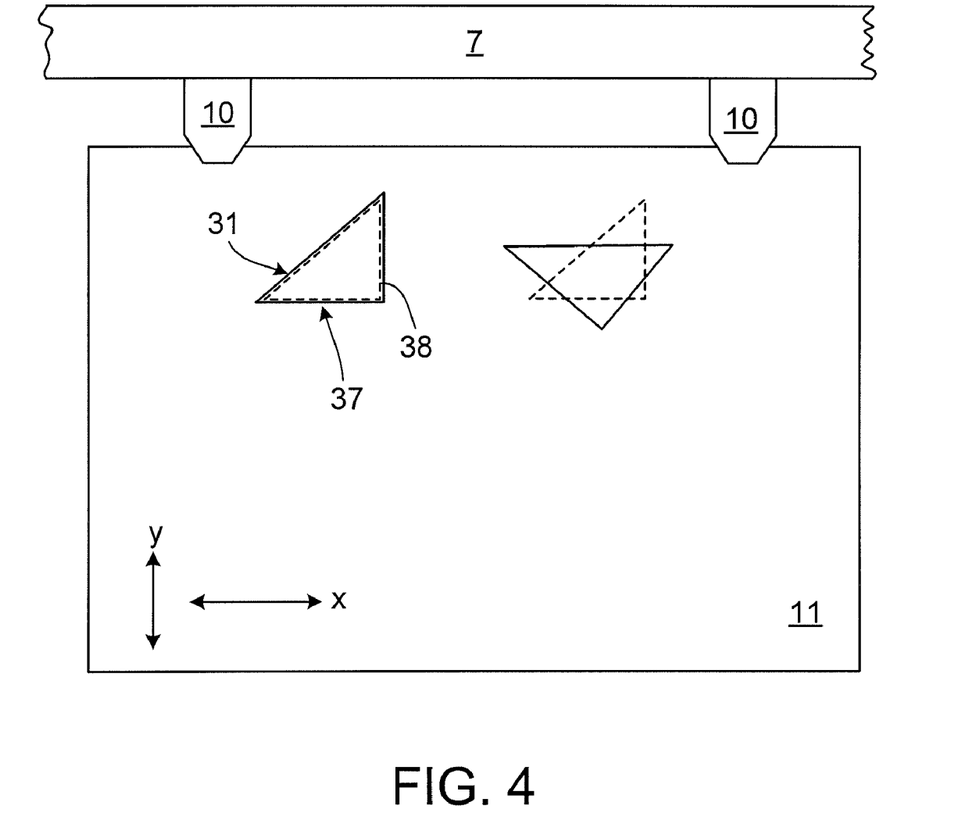
FIG. 4 is an illustration of the operation of the device of FIG. 1 for examining the processing result in a third application and FIGS. 5a, 5b, and 5c are illustrations of the operation of the device of FIG. 1 for examining the processing result in a fourth application.

Accordingly, as shown in FIG. 4, a path 38 of a detection movement can follow the desired contour of the edge 31 of a metal sheet hole or a punched-out portion 37, to determine whether the punched-out portion 37 is orientated correctly or incorrectly with respect to the metal sheet 11.

Figure 5A:
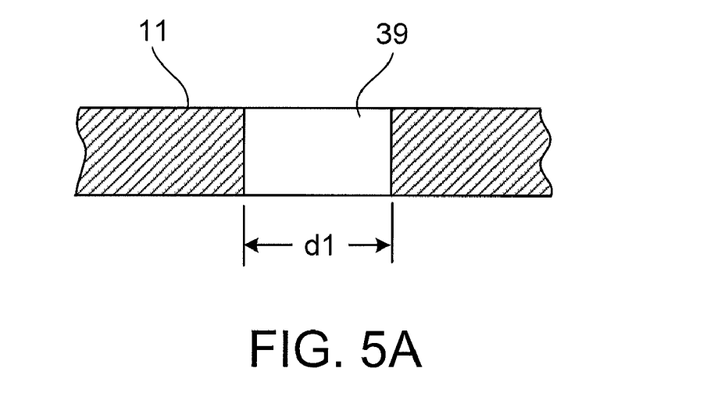
Figure 5B:
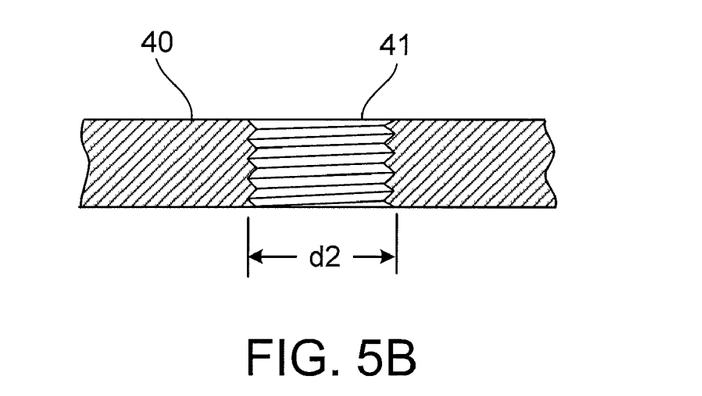
Figure 5C:
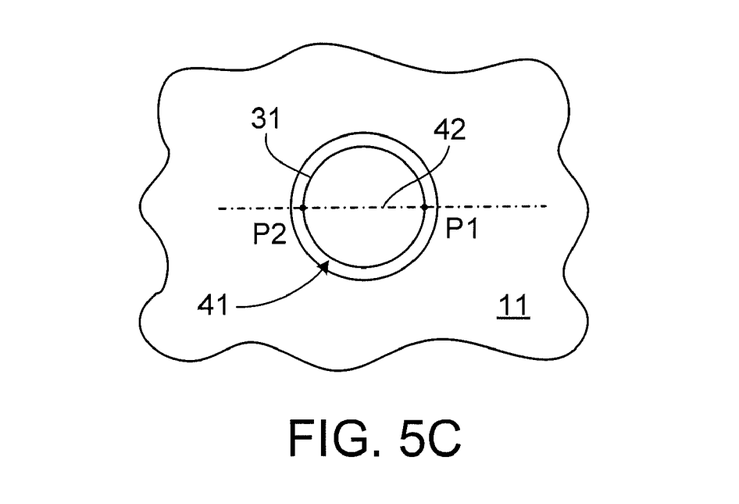

In FIGS. 5a, 5b, and 5c, a metal sheet hole in the form of a punched-out portion 39 is produced first by a punching tool 18 of the mechanical arrangement 1. In FIG. 5a, the circular punched-out portion 39 in the embodiment has a diameter d1. After the punching processing of the metal sheet 11, a thread forming tool 19 is mounted at the upper tool receiving member 14 and the lower tool receiving member 17 in place of the punching tool 18. A thread 40 is then formed in the wall of the punched-out portion 39 by the thread forming tool 19. In FIG. 5b, a metal sheet hole or threaded hole 41 provided with the thread 40 has a core diameter d2.

The core diameter d2 is a few tenths of a millimeter smaller than the diameter d1 for processing reasons. The punched-out portion 39 can also be produced in a completely separate operation, for example, on a processing device, which is different from the mechanical arrangement 1.

To examine the processing result, the metal sheet 11 with the region of the threaded hole 41 is moved relative to the laser beam 29 which is emitted from the transmission and reception unit 22 of the mechanical arrangement 1. A path 42 of the detection movement is indicated as a dot-dash line in FIG. 5c. As discussed in connection with FIG. 2, the actual extent, e.g. the actual diameter of the threaded hole 41, is determined between intersection points P1' and P2'. Subsequently, the determined actual extent is compared with the corresponding desired extent. If that comparison yields that the actual extent of the threaded hole 41 does not have the desired dimension, but instead the dimension d1, this indicates a malfunction of the thread forming operation. A damaged thread forming tool 19 can be the reason for that malfunction. As discussed above, signals can be generated that indicate information about the processing operation based on the comparison between actual and desired configurations. Moreover, the treading process can be modified based on the comparison.

In the applications shown in FIGS. 3, 4, and 5a to 5c, an intervention can be also carried out in the production process of the mechanical arrangement 1 in case an irregular processing result is determined. For example, the drive motors of the coordinate guide unit 6 and the press drive of the press device 13 can be stopped and an error message for the machine operator can be generated.

A number of embodiments of the invention have been described. Nevertheless, it will be understood that various modifications may be made without departing from the spirit and scope of the invention. Accordingly, other embodiments are within the scope of the following claims.

What is claimed is:

1. A method of examining the quality of a metal sheet hole produced from a metal sheet processing operation for the presence of regular or irregular conditions during the metal sheet processing operation, the method comprising:

scanning a detection beam along a processed metal sheet by causing a relative movement between the detection beam and the processed metal sheet having the metal sheet hole;

during the scanning, determining a position of an edge of the metal sheet hole by monitoring the detection beam as the detection beam scans over the metal sheet hole;

determining, based on the determined hole edge position, a geometric configuration of the metal sheet hole;

performing a comparison of the determined geometric configuration of the metal sheet hole with a corresponding specified hole configuration; and sending a signal, based on the comparison, indicating information about the quality of the metal sheet hole, wherein the quality of the metal sheet hole represents the presence of regular or irregular conditions during the metal sheet processing operation, based upon the comparison.

2. The method of claim 1, wherein the detection beam is a light beam.

3. The method of claim 1, wherein the detection beam and the processed metal sheet are moved relative to each other such that a scanned path extends transversely through the metal sheet hole.

4. The method of claim 3, wherein during scanning, the edge of the metal sheet hole is detected at points of intersection of the edge of the metal sheet hole with the path.

5. The method of claim 4, further including determining an actual extent between the detected points of intersection.

6. The method of claim 5, further including comparing the actual extent of the metal sheet hole with a corresponding specified extent.

7. The method of claim 1, further comprising:
scanning a path, that extends transversely through the circular metal sheet hole;
detecting points of intersection of the edge of the circular metal sheet hole and the path,
wherein the metal sheet hole is circular and the determined geometric configuration of the circular metal sheet hole is an actual diameter of the circular metal sheet hole given by the distance between the detected points of intersection and wherein the actual diameter of the circular metal sheet hole is compared with a corresponding specified diameter as a corresponding specified hole configuration.

8. The method of claim 1, wherein the detection beam is scanned relative to the processed metal sheet along a path that extends along the edge of the metal sheet hole, such that at least a partial length of the edge of the metal sheet hole is detected.

9. The method of claim 1, wherein the determined geometric configuration of the metal sheet hole is a configuration of at least a portion of an edge contour of the metal sheet hole.

10. The method of claim 1, wherein the determined geometric configuration of the metal sheet hole is at least one of an actual shape and an actual orientation of at least a portion of an edge contour of the metal sheet hole.

11. The method of claim 10, wherein the at least one of the actual shape and the actual orientation of the edge contour of the metal sheet hole is compared with a corresponding specified shape and with a corresponding specified orientation, respectively.

12. A method of forming specified metal sheet holes in sheet metal, the method comprising:

forming a metal sheet hole by a set of hole forming operation parameters; moving a detection beam across an edge of the formed metal sheet hole to locate a position of the edge based on detecting the detection beam~ at a defined position of the detection beam and of the metal sheet;

determining, based on the edge position location, a characteristic of the formed metal sheet hole;

making a comparison of the determined characteristic of the metal sheet hole to a specified characteristic of the metal sheet hole, wherein making the comparison includes obtaining information about the presence or absence of specified conditions during the metal sheet processing operation; and based upon the comparison, modifying one or more of the hole forming operation parameters for forming a further metal sheet hole.

13. The method of claim 12, further including determining a deviation of the determined characteristic from the corresponding specified characteristic, the deviation being indicative for the absence of regular conditions and performing an intervention to correct for the deviation to provide regular conditions for a succeeding metal sheet processing operation.

14. The method of claim 12, wherein forming a metal sheet hole includes applying a punching tool to the sheet metal for generating the metal sheet hole and wherein modifying the hole forming operation parameter includes exchanging the punching tool.

15. The method of claim 14, wherein making the comparison provides information about at least one of the punching tool being the correct punching tool, the punching tool being in an acceptable operating condition, the punching tool being worn, and the punching toll being broken.

16. The method of claim 12, further including applying a threading tool for generating a thread in the metal sheet hole, and the device for examining the operating condition is configured to derive information about the operating condition of the threading tool.

17. The method of claim 16, wherein the information includes at least one of the threading tool being the correct threading tool, the threading tool being in an acceptable operating condition, the threading tool being worn, and the threading tool being broken.

18. A hole forming machine comprising:
a tool operable to form a metal sheet hole in sheet metal;
a beam source operable to move a hole detection beam across an edge of a metal sheet hole formed by the tool;
a beam detector responsive to the hole detection beam to generate a signal indicating beam detection;
a hole edge evaluator to:
receive the signal from the beam detector;
determine a position of an the edge of the metal sheet hole and a geometric configuration of the metal sheet hole, based on the received signal;
make a comparison of the geometric configuration of the metal sheet hole to a corresponding specified hole configuration; and
send a signal indicative of an irregular condition of one or more hole forming operation parameters.

* * * * *

UNITED STATES PATENT AND TRADEMARK OFFICE
CERTIFICATE OF CORRECTION

| | |
|---|---|
| PATENT NO. | : 8,098,923 B2 |
| APPLICATION NO. | : 12/047662 |
| DATED | : January 17, 2012 |
| INVENTOR(S) | : Peter Bytow |

It is certified that error appears in the above-identified patent and that said Letters Patent is hereby corrected as shown below:

Column 11, line 30 (Claim 7, line 2) delete "path," and insert --path--.

Column 11, line 32 (Claim 7, line 4) before "metal" delete --circular--.

Column 12, line 4 (Claim 12, line 6) delete "beam~" and insert --beam--.

Column 12, line 7 (Claim 12, line 9) delete "position location," and insert --position,--.

Column 12, line 33 (Claim 15, line 5) delete "toll" and insert --tool--.

Column 12, line 52 (Claim 18, line 9) delete "an the" and insert --the--.

Signed and Sealed this
Seventh Day of August, 2012

David J. Kappos
*Director of the United States Patent and Trademark Office*